United States Patent
Fox et al.

(10) Patent No.: US 6,984,391 B2
(45) Date of Patent: Jan. 10, 2006

(54) COMPOSITIONS AND METHODS FOR DELIVERY OF SKIN COSMECEUTICALS

(76) Inventors: Charles Fox, 39-08 Tierney Pl., Fair Lawn, NJ (US) 07410; Terrence S. McGrath, c/o Hydron Technologies, Inc., 2201 W. Sample Rd., Bldg. 9 Ste 7B, Pompano Beach, FL (US) 33073

( * ) Notice: Subject to any disclaimer, the term of this patent is extended or adjusted under 35 U.S.C. 154(b) by 380 days.

(21) Appl. No.: 10/366,845

(22) Filed: Feb. 14, 2003

(65) Prior Publication Data

US 2003/0165552 A1  Sep. 4, 2003

Related U.S. Application Data

(60) Provisional application No. 60/357,466, filed on Feb. 15, 2002.

(51) Int. Cl.
*A61K 31/74* (2006.01)
(52) U.S. Cl. ........................ 424/401; 514/844; 514/846; 424/78.03
(58) Field of Classification Search ................ 424/401; 514/844, 846
See application file for complete search history.

(56) References Cited

U.S. PATENT DOCUMENTS 5,001,156 A    3/1991   Philippe et al. ............... 514/55
5,073,372 A *  12/1991  Turner et al. ............... 424/401
5,997,887 A *  12/1999  Ha et al. ..................... 424/401

OTHER PUBLICATIONS

Berardesca, E., et al., "Differences in stratum corneum pH . . . " Brit. J. Dermat. 139: 855-857 (19998).
Kligman, A., in Dry Skin and Moisturizers, Ed. Loden and Maibach, CRC Press, Boca Raton, 2000, p. 8.
Mauro, T. et al., "Barrier recovery is impeded at neutral . . . " Arch Dermatol Res 290: 215-222 (1998).

* cited by examiner

*Primary Examiner*—Thurman K. Page
*Assistant Examiner*—Sharon Howard
(74) *Attorney, Agent, or Firm*—Edwards & Angell, LLP

(57) ABSTRACT

New cosmetic compositions are disclosed that are effective both as moisturizers and skin sloughing agents. The compositions contain neutralized weak organic acids that when applied over time to the skin in appropriate formulations will gradually increase in acidity to pH 5.5 or less, for example about pH 4.5, without causing skin irritation while exhibiting increasing activity in skin renewal effects.

29 Claims, 1 Drawing Sheet

COMPOSITIONS AND METHODS FOR DELIVERY OF SKIN COSMECEUTICALS

This application claims the benefit of Provisional Application No. 60/357,466, filed Feb. 15, 2002.

BACKGROUND ART

1. Field of the Invention

The invention concerns compositions and methods for formulating and delivering cosmeceutical skin preparations. The disclosed compositions are particularly adapted for delivery of acidic agents for skin renewal and treatment agents.

2. Description of Related Art

Human skin acts as a protective barrier to both physical and chemical insults. The properties of the cutaneous layer are important to the cosmetic industry in developing effective and safe skin preparations in addition to medical concerns in treating damage to the skin surface in conditions such as acne.

The epidermal surface is acidic and has been the subject of studies on epidermal permeability and formation. The chemistry and function of dry skin and moisturizers has been extensively reviewed (Loden and Howard, eds, 2000) in the context of understanding the factors involved in developing skin moisturizers and protective formulations.

Skin homeostasis normally is maintained at about pH 5 allowing lipid barrier repairs. At more neutral or alkaline pH, skin repair is inhibited (Mauro, 1998). Studies have shown that there are racial differences in the stratum corneum pH gradient at least with respect to the surface layers. Significant differences between Caucasian and black African-American skin was reported by Berasdesca, et al. (1998), although no differences were found in the deeper stratum corneum layers.

Mauro et al. states that the skin's lipid barrier is impeded at neutral pH, independent of ionic effects. Epidermal permeability barrier homeostasis requires the post-secretory processing of polar lipid precursors into nonpolar lipid products within the stratum corneum (SC) interstices by a family of lipid hydrolase enzymes. A specific requirement for beta-glucocerebrosidase (beta-GlcCer'ase), which exhibits a distinct optimum acidic pH, is particularly well documented. The investigators sought to determine whether the recovery of the barrier after acute insults requires acidification of the SC. They examined permeability barrier recovery by assessing changes in transepidermal water loss (TEWL), SC membrane ultrastructure utilizing ruthenium tetroxide ($RuO_4$) postfixation, and beta-GlcCer'ase activity by in situ zymography at an acidic vs. neutral pH. Barrier recovery proceeded normally when acetone-treated skin was exposed to solutions buffered to an acidic pH. In contrast, the initiation of barrier recovery was slowed when treated skin was exposed to neutral or alkaline pH, regardless of buffer composition. In addition, enhancement of the alkaline buffer-induced delay in barrier recovery occurred with $Ca^{2+}$ and $K^+$ inclusion in the buffer. Moreover, the pH-dependent alteration in barrier recovery appeared to occur through a mechanism that was independent of $Ca^{2+}$ or $K^+$ controlled lamellar body secretion, since both the formation and secretion of lamellar bodies proceeded comparably at pH 5.5 and pH 7.4. Exposure to pH 7.4 (but not pH 5.5) resulted in both the persistence of immature, extracellular lamellar membrane structures, and a marked decrease in the in situ activity of beta-GlcCer'ase. These results suggest first that an acidic extracellular pH is necessary for the initiation of barrier recovery, and second that the delay in barrier recovery is a consequence of inhibition of post-secretory lipid processing.

Kligman (2000) states ". . . our concept of humectants (as moisturizers) falls short of explaining how they work. It is worth repeating that used alone they are not much good. It is only when they are properly formulated with other ingredients that their potential benefits are realized. Other factors such as pH also have to be taken into account, because proteases which lead to orderly desquamation of horny cells within the stratum corneum are activated only at acid pHs of 4 to 5. Also the various hydrolytic enzymes, which are found in the stratum corneum and which are essential to the formation of the intercorneocyte lipids that establish the impermeability of the barrier, are activated only at acid pHs" (Kligman, 2000).

Feingold and Elias (2000) state that the epidermal surface has been known for many years to be acidic, but the role of this acidic pH of the stratum corneum in barrier homeostasis was unknown. It is well recognized that $\beta$-glucocerebrosidase is most active at pH 5.5. Recently, we have examined barrier recovery of an acidic vs. neutral pH. Barrier recovery proceeded normally when acetone treated skin was exposed to solutions buffered to an acidic pH. In contrast, barrier recovery was delayed when treated skin was exposed to neutral or alkaline pH regardless of buffer composition" (in Dermatology, eds. Loden and Maibach, 2000). These results indicate that an acidic extracellular pH in the SC is required for normal extracellular lipid processing and normal barrier homeostasis.

The majority of marketed skin treatment preparations use emulsifying agents that are non-volatile and accordingly remain on the skin until removed by cleansing. Most facial care cosmetics are formulated with about 5–7% emulsifying agents, at a pH of 6.5–8.0 to insure product stability, and contain on average about 75% water. After application to the skin the water used in the formulation evaporates off the skin quickly, leaving up to approximately a 20% concentration of emulsifying agents on the skin. This high level of emulsifying agent is capable of emulsifying the natural lipids in the skin which can be removed on cleansing the skin. The net result is detrimental to the skin for two reasons: the residual pH of 6.5 to 8.0 is not favorable for the repair of the skin's lipid barrier layer and the residual high level of emulsifying agents is conducive to removal of the natural lipids in the skin leading to an even drier skin condition. The stress of the emulsifying agent residue causes overstimulation of the skin, increased oil production, irritation and blemishes. Stronger emulsions are difficult to neutralize for older skin and sensitive skin. Harsh emulsifiers may actually damage skin by dissolving the skin's protective lipid barrier, which is essential to healthy looking skin. Additionally, perspiration may remove the active ingredients deposited on the skin.

DEFICIENCIES IN THE PRIOR ART

The inventors have observed that an acidic skin care agent is desirable for the reasons given above, but many acidic agents that have been used in skin products have a pH low enough to cause irritation or slight burning. The irritation and burning can be cumulative over repeated application. The acids are effective at low pH, however, they are not available in formulations for periods of time of at least several hours at optimal effective pHs. A stable shelf-life is necessary for skin care formulations, which generally requires a pH of no lower than 6.0. A pH of 6.0 or more insures that the product is stable, but is too high to promote effective rebuilding of the skin's protective barrier.

SUMMARY OF THE INVENTION

The invention recognizes the need to provide an environment of below pH 5.5, and preferably between about pH 4.5 and 5.0 to promote activity of the skin enzymes involved in repairing a damaged lipid skin barrier.

The invention addresses the problem of providing an ideal pH for cosmeceuticals and skin treatments. This is accomplished by providing an ammonium salt of a selected weak organic acid to the skin in a formulation that allows slow evaporation after skin contact, resulting in release of ammonia and a gradual decrease in pH at or below 5.5 The decrease in pH may take place over several hours. Active ingredient delivery of pharmaceutical ingredients and/or skin sloughing is enhanced as the pH becomes more acidic, but there is no irritation because the decrease in pH is gradual. At some point the pH of the parent acid is reached, adding a measure of control over the final pH.

As used herein, the disclosed preparations and formulations are termed cosmeceuticals, a hybrid term incorporating the concept of improving skin appearance by application of active ingredients that often serve a therapeutic role. Certain of the particular formulations disclosed have application in treatment of skin conditions with over the counter (OTC) drugs, such as the use of salicylic acid for acne treatment. The disclosed formulations provide, among other benefits, a method of controlling pH of salicylic acid on the skin to avoid irritation and burning and by causing a gradual lowering of pH from the neutral value at the initial application.

The disclosed novel product delivery system has many advantages over conventional products in regard to safety, efficacy and longevity of action.

There are many weak organic acids that are beneficial to the skin, such as salicylic acid, glycolic acid, lactic acid, malic acid, citric acid, tartaric acid and the like but which have a very low pH and can be irritating. Salicylic acid is a beta hydroxy acid and is an approved drug at 2% for the treatment of acne. Other acids include alpha and mixed alpha and beta-hydroxy acids that are used to slough off the top dead layers of the skin to improve skin appearance.

Selected acids are formulated into vehicles in the form of solutions, lotions, and/or creams that are well recognized for use in the preparation of skin products. The final products are adjusted to a pH value of 6.5–6.9 with an aqueous ammonia solution. This results in the formation of the ammonium salt(s) so neutralized. It is well known that certain salts of alpha hydroxy acids such as the sodium, potassium, ammonium, diethanolamine, triethanolamine etc. salts are humectants and when applied to the skin they are safe and non-irritating and are powerful skin moisturizers; but because the pH is at neutrality, these salts remain active only as humectants and will not enhance skin sloughing of scaly dry skin or enhance skin turnover. However, when the salts applied are the ammonium salts, as in the present invention, after application to the skin the ammonia gradually evaporates from the product, the pH drops and the moisturizer turns into an active acid for enhancing skin sloughing and turnover and in the case of salicylic acid becomes an active agent for the treatment of acne. The advantage of this system is that the pH drop occurs over time, typically three to four hours and so the product is never irritating to the skin and the activity increases with time.

It is also possible to build into these systems salts of skin protective polymers that are water soluble at pH 6 to pH 7 but which become insoluble at pH values below pH 5. Thus ammonium carboxymethyl cellulose, ammonium alginate, ammonium carragheenate, ammonium polyacrylate, ammonium VA/Acrylate and the like are water soluble but after application to the skin the ammonia evaporates and a thin layer of water insoluble polymer is left on the skin which acts as a barrier to protect the skin, enhances skin moisturization and, because it is water insoluble, holds other important ingredients in contact with the skin.

There is one further major advantage that accrues in using the ammoniated system. It has been shown that the skin enzymes involved in repairing a damaged lipid skin barrier are only active at a pH of below 5.5. Almost every skin care preparation on the market today is at a pH of 6.5–7.5 and remains at this pH for as long as it remains on the skin thus interfering with the enzymes required for rebuilding the protective lipid barrier. In the disclosed compositions, the ammonia evaporates and the pH reaches the optimum level for enzymatic activity and skin barrier repair.

In certain embodiments, a self-adjusting emulsifier may be employed. As the emulsifier in the formulation evaporates, the composition self-adjusts to a lower pH which will typically be in the range of 3.5–5.5 matching the stratum corneum pH required for haling and enzyme production to repair the lipid barrier.

There are two types of emulsions: oil in water and water in oil. Formulations can be created to deliver 100% of the therapeutic ingredients on application to the skin and hold the ingredients when a polymer complex is used. Polymer based moisturizers create a protective barrier on the skin that captures moisture normally lost by the skin but at the same time allow the skin to readily exchange oxygen and carbon dioxide, unlike oil based moisturizers. The moisture cushion allows water to soften the skin.

The basic compositions may include numerous other ingredients, depending on the requirements of a particular skin type. Vitamins such as vitamin A palmitate, pro-vitamin B-5, vitamin E, vitamin D3 and vitamin C are illustrative of beneficial vitamins that may be added. Herbal and botanicals may also be included with the ammonium salts, including green tea, aloe vera, ivy extract chamomile, watercress, silk, sea kelp, meadowsweet, ginkgo biloba, spirulina maxima, passion flower, witch hazel, pea extract, algae extract, apple, sugar cane, avocado oil, jojoba oil and evening primrose oil.

Delivery may be formulated in liposomes, ceramide III, triclosan, avobenzone, oxybenzone or in other numerous ways accepted in the art for formulating cosmeceuticals.

DETAILED DESCRIPTION OF ILLUSTRATIVE EMBODIMENTS

Figure 1:
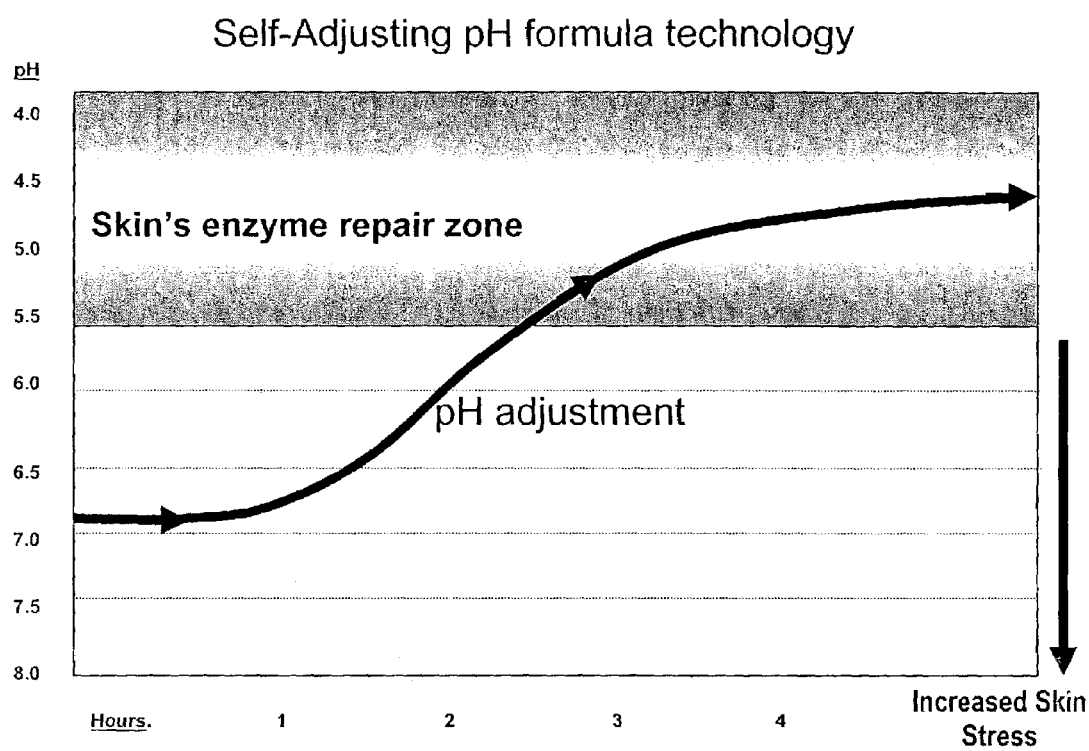
FIG. 1 shows the natural pH repair zone for skin.
Figure 2:
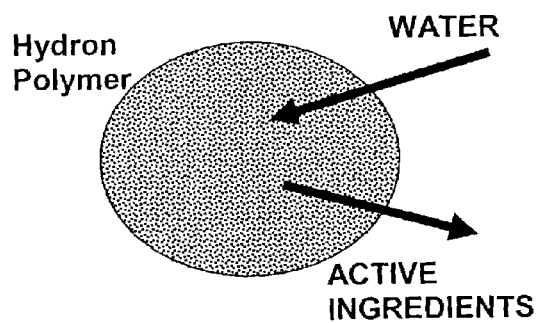
FIG. 2 schematically illustrates the moisture uptake by a polymer layer at the skin surface and concomitant release of active ingredients.

The present invention relates to cosmetic moisturizing preparations that adjust from higher to lower pH after application. These formulations typically provide a pH level of about 4.5 by incorporating a fatty acid salt as a major ingredient. The salt is converted at least in part to a fatty acid which lowers the pH at the skin surface. This is illustrated in Table 1 where pH changes for selected moisturizing creams from different brands are compared.

Most moisturizers are formulated and packaged for long shelf life. Initially the pH is adjusted to about 6.0–7.5 to provide the stability required. This is accomplished by providing an ammonium salt of a selected weak organic acid to the skin in a formulation that allows slow evaporation after skin contact, resulting in release of ammonia and a gradual decrease in pH at or below 5.5 The decrease in pH may take place over several hours. Active ingredient delivery of pharmaceutical ingredients and/or skin sloughing is enhanced as the pH becomes more acidic, but there is no irritation because the decrease in pH is gradual. At some point the pH of the parent acid is reached, adding a measure of control over the final pH.

EXAMPLES

Example 1

Skin Moisturizing and Sloughing Preparation

| | Percent (w/w) |
|---|---|
| Part 1 | |
| Stearic Acid | 2.55 |
| Cetyl Alcohol | 1.70 |
| Glyceryl Stearate | 1.25 |
| Isopropyl Stearate | 0.42 |
| Caprylic/Capric Triglyceride | 0.25 |
| Lanolin | 0.42 |
| Part 2 | |
| Deionized Water | qs 100.00 |
| Glycolic Acid (70%)* | 7.00 |
| Ammonium Hydroxide (28%) | qs to pH 6.7 |
| Part 3 | |
| Propylene Glycol | 7.50 |
| SD Alcohol 40-2 | 5.00 |
| Polyhydroxyethylmethacrylate | 0.50 |
| Steareth-20 | 0.02 |
| Part 4 | |
| Germaben II (ISP) | 1.00 |
| Part 5 | |
| Fragrance | 0.10 |

Example 2

Skin Facial Moisturizing and Sloughing Preparation

| | Percent (w/w) |
|---|---|
| Part 1 | |
| Octyl Methoxy Cinnamate | 7.00 |
| Benzophenone-3 | 3.00 |
| Avobenzone | 2.00 |
| Stearic Acid | 2.30 |
| Cetyl Alcohol | 1.50 |
| Glyceryl Stearate | 1.50 |
| Dimethicone | 1.00 |
| Tocopheryl Acetate Cosmetic Grade | 0.50 |
| C$_{12-15}$ Alkyl Benzoate | 0.35 |
| Stearoxytrimethylsilane | 0.25 |
| Part 2 | |
| Vitamin A Palmitate | 0.10 |
| Tetrahexadecyl Ascorbate | 0.10 |
| Part 3 | |
| Deionized Water | qs 100.00 |
| Lactic Acid (88%)* | 5.00 |
| Disodium Edetate | 0.20 |
| Part 4 | |
| Deionized Water | 9.80 |
| Propylene Glycol | 7.50 |
| SD Alcohol 40-2 | 5.00 |
| Polyhydroxyethylmethacrylate | 0.50 |
| Aloe Vera Gel (200X) | 0.10 |
| Steareth-20 | 0.02 |
| Part 5 | |
| Ammonia Solution Strong (27%) (26° Baume) | qs to pH 6.7–6.9 |

Example 3

Acne Moisturizing and Treatment Cream

| | Percent (w/w) |
|---|---|
| Caprylic/Capric Triglyceride | 5.00 |
| Glyceryl Stearate | 3.00 |
| Salicylic Acid* | 2.00 |
| Cetyl Alcohol | 1.50 |
| Stearic Acid | 1.30 |
| Beeswax | 1.00 |
| Cholesterol | 0.25 |
| BHT | 0.05 |
| Part 2 | |
| Deionized Water | 47.17 |
| Propylene Glycol | 5.00 |
| Sodium Hyaluronate | 3.00 |
| Sodium PCA | 2.00 |
| Saccharide Isomerate | 1.00 |
| Disodium Edetate | 0.20 |
| Part 3 | |
| Deionized Water | 9.80 |
| Propylene Glycol | 7.50 |
| SD Alcohol 40-2 | 5.00 |
| Polyhydroxyethylmethacrylate | 0.50 |
| Aloe Vera Gel (200X) | 0.10 |
| Steareth-20 | 0.02 |
| Part 4 | |
| Ammonia Solution Strong (27%) (26° Baume) | qs to pH 6.7–6.9 |

*While the examples shown above utilize glycolic, lactic and salicylic acids, this does not preclude the use of other hydroxy or non-hydroxy acids having a moisturizing, skin sloughing or skin treatment effect.

Ammonium stearate was used as the emulsifying agent. Glycolic acid was neutralized with ammonia to form the ammonium salt. The salt was then formulated into a pharmaceutically acceptable cream selected for non-irritation to the skin and typically used in preparing cosmetic formulations. An all over moisturizer was prepared (Example 1), with similar preparations prepared for the face (Example 2), as an acne treatment cream (Example 3), for the fragile eye area (Example 4) and as a night cream (Example 5). The composition of Examples 1–3 is given above. For Examples 4 and 5, the different preparations used different concentrations of inactive ingredients that are well known in the art for producing moisturizing creams. Upon application to the skin, the ammonia gradually evaporated to form glycolic acid. The acid began sloughing of dead cells with greater activity over a period of 3–4 hours as the pH of the composition gradually decreased over this period to about 4.5.

Table 1 illustrates the change in pH over time of several cosmetic products by comparison to the disclosed product. It can be seen that the pH of Examples 1–4 decreases to 4.5 and remains at that level for several hours in contrast with comparable products whose pH shows little change from neutral.

TABLE 1

| Product | pH* | | | | |
|---|---|---|---|---|---|
| | Initial | 1 Hour | 2 Hours | 3 Hours | 8 Hours |
| Vaseline** Intensive Care Advanced Healing Lotion (Lot 04219PP10) | 7.5 | 7.5 | 7.5 | 7.5 | 7.5 |
| Vaseline** Intensive Care Dry Skin Lotion (Lot 67999L) | 7.0 | 7.0 | 7.0 | 7.0 | 7.0 |
| Lubriderm** Skin Therapy (Lot 67999L) | 7.5 | 7.5 | 7.5 | 7.5 | 7.5 |
| Neutrogena** Moisture for Sensitive Skin (lot 1L9) | 7.5 | 7.5 | 7.5 | 7.5 | 7.5 |
| Ponds** Nourishing Moisturizer Lotion (Lot 01190H02) | 6.5 | 6.5 | 6.5 | 6.5 | 6.5 |
| Neutrogena** Intensified Day Moisture (Lot 1M9) | 7.0 | 7.0 | 7.0 | 7.0 | 7.0 |
| L'Oreal** Active Daily Moisture Lotion (Lot PV108) | 6.0 | 6.0 | 6.0 | 6.0 | 6.0 |
| Nivea** Visage (Lot 99169) | 7.0 | 6.5 | 6.5 | 6.5 | 6.5 |
| Night of Olay** Lot 916OH | 7.0 | 6.5 | 6.5 | 6.5 | 6.5 |
| Nivea** Q-10 Cream (Lot 92840851) | 7.0 | 7.0 | 7.0 | 7.0 | 7.0 |
| Olay** Activating Hydration Lotion (Lot 901911) | 7.0 | 7.0 | 7.0 | 7.0 | 7.0 |
| Estee Lauder** Resilience (Lot CB9) | 6.0 | 6.0 | 6.0 | 6.0 | 6.0 |
| Clinique** Dramatically Moisturizing Lotion (Lot 037) | 7.5 | 7.5 | 7.5 | 7.5 | 7.5 |
| Lancôme** Renergic Antiwrinkle Cream (Lot 0257) | 6.0 | 6.0 | 6.0 | 6.0 | 6.0 |
| Example 1 | 7.0 | 5.5 | 5.0 | 4.5 | 4.5 |
| Example 2 | 7.0 | 5.8 | 5.0 | 4.5 | 4.5 |
| Example 3 | 7.0 | 5.5 | 5.0 | 4.5 | 4.5 |
| Example 4 | 7.0 | 5.5 | 5.0 | 4.5 | 4.5 |
| Example 5 | 7.0 | 5.5 | 5.0 | 4.5 | 4.5 |

*ColorpHast pH 0–14 pH paper, EM Science, Gibbstown, NJ 08027 was used for this test
**Registered Trademarks The examples of the present invention were tested in 8 and 12 hour clinical studies, which proved extended performance as well as a reduction in pH. After 8 hours in a sweat booth, only 4% of the moisturizer had been removed from the skin. In addition, immersion testing proved outstanding results. At the end of the day, positive moisturization was felt, whereas most formulas fail in a few hours. The example products did not need to be altered for oily, normal, or dry skin, as the controlled release of the acids were found to balance and normalize all skin types, even the most sensitive skin.

REFERENCES

Berardesca, E., Pirot, F. Singh, M. and Maibach, H. "Differences in stratum corneum pH gradient when comparing white Caucasian and black African-American skin" Brit. J. Dermatology, 139, 855–857 (1998).
Feingold, K. R. and Elias, P. M. in Dermatology: Clinical & Basic Science Series, eds. Marie Loden and Howard I. Maibach, CRC Press, 45–58, 2000
Kligman, A. in Dry skin and Moisturizers, Ed. Loden and Maibach, CRC Press, Boca Raton, 2000, p. 8
Mauro, T. Arch Dermatol. Res 290(4): 215–222, 1998

What is claimed is:

1. A composition comprising an ammonium salt of a weak organic acid combined with a time release polymer base formulation wherein the composition releases ammonia when in skin contact to provide a gradual decrease in pH to 5.5 or less.

2. The composition of claim 1, wherein the pH of the composition gradually decreases to between 2.0 and 5.0 when in skin contact.

3. The composition of claim 2, wherein the pH of the composition gradually decreases to between 4.0 and 4.5 when in skin contact.

4. The composition of claim 1, wherein the weak organic acid is selected from salicylic acid, glycolic acid, lactic acid, malic acid, citric acid, and tartaric acid.

5. The composition of claim 1, wherein the weak organic is an alpha or beta hydroxy acid.

6. The composition of claim 5, wherein the beta hydroxy acid is salicylic acid.

7. The composition of claim 1, wherein the time release polymer base formulation is pharmaceutically acceptable.

8. The composition of claim 1, wherein said formulation is a solution, lotion or cream.

9. A method of enhancing skin sloughing, comprising formulating a selected organic weak acid with a pharmaceutically acceptable emulsifying agent, neutralizing the acid with ammonia to a pH of 6.5–6.9 to form a dispersed ammonium salt, applying said ammonium salt to skin wherein the pH gradually lowers to 5.5 or less as ammonia evaporates causing a gradual enhancement of skin sloughing.

10. The method of claim 9, wherein the pH of the composition gradually decreases to between 2.0 and 5.0 when in skin contact.

11. The method of claim 10, wherein the pH of the composition gradually decreases to between 4.0 and 4.5 when in skin contact.

12. The method of claim 9, wherein the emulsifying agent is a volatile emulsifying polymer that evaporates over a period of time to leave a water insoluble polymer on skin surface.

13. The method of claim 9, wherein the weak organic acid is selected from the group consisting of salicylic acid, glycolic acid, lactic acid, malic acid, citric acid and tartaric acid.

14. The method of claim 9, wherein the pH is lowered over a period of 3–4 hours.

15. The method of claim 9, wherein the weak organic acid is an alpha or beta hydroxy acid.

16. The method of claim 15, wherein the beta hydroxy acid is salicylic acid.

17. The method of claim 9, further comprising a polymer that is water soluble pH 6 to 7 wherein the polymer becomes insoluble at a pH 5 and below pH 5.

18. The method of claim 17, wherein the water soluble polymer is ammonium carboxymethyl cellulose, ammonium alginate, ammonium carragheenate, ammonium polyacrylate, or ammonium VA/Acrylate.

19. A kit comprising the composition of claim 1, in suitable container form and directions for applying said composition for skin moisturization and sloughing.

20. The kit of claim 19, wherein the composition is ammonium salicylate in a skin protective polymer.

21. The kit of claim 20, wherein the skin protective polymer is water soluble at neutral pH and insoluble at pH 5 and below pH 5.

22. The kit of claim 20, wherein the skin protective polymer is ammonium carboxymethyl cellulose, ammonium alginate, ammonium carragheenate, ammonium polyacrylate, or ammonium VA/Acrylate.

23. A method for treating acne, comprising applying an ammonium salt of salicylic acid dispersed in a formulation with an emulsifying agent and a lipid with sufficient water to allow gradual release of ammonia when in skin contact wherein the pH of the skin surface gradually lowers to a pH of 5.5 or less.

24. The method of claim 23, wherein the skin surface pH gradually decreases to between 2.0 and 5.0 when the composition is in skin contact.

25. The method of claim 24, wherein the skin surface pH gradually decreases to between 4.0 and 4.5 when the composition is in skin contact.

26. The method of claim 23, wherein the emulsifying agent is combined with a polymer and wherein the emulsifying agent evaporates over a period of time to leave a water insoluble emollient and/or polymer on the skin surface.

27. A method of enhancing skin sloughing, comprising formulating a selected organic weak acid with a pharmaceutically acceptable emulsifying agent, neutralizing the acid with ammonia to a pH of 6.5–6.9 to form a dispersed ammonium salt, applying said ammonium salt to skin wherein the pH gradually lowers to 5.5 or less as ammonia evaporates causing a gradual enhancement of skin sloughing.

28. The method of claim 27, wherein the pH gradually decreases to between 2.0 and 5.0 when the ammonium salt is in skin contact.

29. The method of claim 28, wherein the pH gradually decreases to between 4.0 and 4.5 when the ammonium salt is in skin contact.

* * * * *